US008911959B2

(12) United States Patent
Lake et al.

(10) Patent No.: US 8,911,959 B2
(45) Date of Patent: Dec. 16, 2014

(54) METHODS OF DETECTION OF *COCCIDIOIDES* SPECIES IN BODILY FLUID (75) Inventors: Douglas Lake, Scottsdale, AZ (US); Kwasi Antwi, Queen Creek, AZ (US); Janis E. Blair, Phoenix, AZ (US)

(73) Assignees: Arizona Board of Regents, a body corporate of the State of Arizona Acting for and on behalf of Arizona State University, Scottsdale, AZ (US); Mayo Foundation for Medical Education and Research, Rochester, MN (US)

(*) Notice: Subject to any disclaimer, the term of this patent is extended or adjusted under 35 U.S.C. 154(b) by 0 days.

(21) Appl. No.: 13/608,966

(22) Filed: Sep. 10, 2012

(65) Prior Publication Data

US 2013/0164764 A1 Jun. 27, 2013

Related U.S. Application Data

(60) Provisional application No. 61/532,936, filed on Sep. 9, 2011.

(51) Int. Cl.

| | |
|---|---|
| *G01N 33/569* | (2006.01) |
| *G01N 33/53* | (2006.01) |
| *C12N 5/07* | (2010.01) |
| *C12N 5/16* | (2006.01) |
| *A61K 39/00* | (2006.01) |
| *A01N 63/00* | (2006.01) |
| *A01N 63/04* | (2006.01) |
| *A01N 65/00* | (2009.01) |
| *A61K 49/00* | (2006.01) |
| *G01N 33/68* | (2006.01) |
| *C07K 14/37* | (2006.01) |

(52) U.S. Cl.

CPC ................ *G01N 33/68* (2013.01); *C07K 14/37* (2013.01); *G01N 33/56961* (2013.01); *G01N 2800/52* (2013.01)

USPC ........ 435/7.31; 435/7.1; 435/331; 424/274.1; 424/93.5; 424/9.1

(58) Field of Classification Search

CPC .............. A61K 38/03; A61K 39/0002; A61K 39/39558; A61K 2300/00; A61K 38/212; A61K 39/12; A61K 39/3955; A61K 8/25; A61K 2039/54; A61K 2800/31; A61K 38/164; A61K 38/21; A61K 38/38; A61K 39/092; A61K 47/42; A61K 47/48469; A61K 47/48561; A61K 47/48569; A61K 48/00; A61K 8/0279; A61K 8/04; A61K 8/402; A61K 8/31; A61K 8/345; A61K 8/37; A61K 8/375; A61K 8/585; A61K 8/8111; A61K 8/8117; A61K 8/891; A61K 9/0019; A61K 9/0073; A61N 1/3968; A61N 1/3937; A61N 1/3975; A61N 1/3993; A61N 1/37211; A61N 1/3925; A61N 1/3611; A61N 1/36117; A61N 1/36139; A61N 1/3625; A61N 1/37282; A61N 1/39; A61N 1/3931; A61N 1/3962; A61N 1/3987; A61N 7/00; G06F 1/1632; G06F 12/00; G06F 11/006; G06F 11/1044; G06F 11/108; G06F 11/2025; G06F 11/2038; G06F 11/2046; G06F 11/2094; G06F 12/0246; G06F 13/102; G06F 15/00; G06F 17/30088; G06F 17/30194; G06F 17/30233; G06F 17/30283; G06F 19/20; G06F 19/3418; G06F 19/70; G06F 1/206; G06F 1/26; G06F 3/0304; G06F 3/0428; G06F 3/06; G06F 3/067; G06F 9/45533; G06F 9/4856; C12Q 1/6895; C07K 14/37; G01N 2001/00; G01N 33/48; G01N 33/50

See application file for complete search history.

(56) References Cited

U.S. PATENT DOCUMENTS 7,078,037 B2 * 7/2006 Galgiani et al. ........... 424/185.1
2003/0027231 A1 2/2003 Bryden et al.

FOREIGN PATENT DOCUMENTS

WO WO 2008-154619 A1 12/2008

OTHER PUBLICATIONS

Lake et al., Identification of peptides in plasma from Coccidioides by mass spectrometry, Proceedings of the 55th Annual Coccidioidomycosis Study Group Meeting, Apr. 2011; pp. 1-26.*

Shubitz, Lisa F., et al., "Coccidioidomycosis: A Diagnostic Challenge," Clinical Techniques in Small Animal Practice, pp. 220-226, vol. 20, No. 4, 2005.

Ampel, M.D., Neil M., "Coccidioidomycosis: A Review of Recent Advances," Clinics in Chest Medicine, Jun. 2009, pp. 241-251, vol. 30, No. 2.

Alexander, Barbara D., et al., "Contemporary Tools for the Diagnosis and Management of Invasive Mycoses," Laboratory Tools for Invasive Mycosis, Clinical Infectious Disease, Aug. 2006, pp. S15-S27, vol. 43, Supp. 1.

Durkin, Michelle, et al., "Diagnosis of Coccidioidomycosis with Use of the Coccidioides Antigen Enzyme Immunoassay," Coccidioides Antigen Immunoassay, Clinical Infectious Disease, Oct. 2008, pp. e69-e73, vol. 47, No. 8.

Marinach-Patrice, Carine, et. al., "Rapid Species Diagnosis for Invasive Candidiasis Using Mass Spectrometry," PLoS ONE, Jan. 2010, p. e8862, vol. 5, No. 1.

* cited by examiner

*Primary Examiner* — Gary Nickol
*Assistant Examiner* — Lakia Tongue
(74) *Attorney, Agent, or Firm* — Quarles & Brady LLP; Gavin J. Milczarek-Desai

(57) ABSTRACT

Coccidioidomycosis (Valley Fever) is currently diagnosed by relying on infected individuals (humans, dogs, etc.) to generate antibodies against the fungus. Since the immune response against Valley Fever can be delayed or absent in many cases, methods that detect a polypeptide or peptide component of the *Coccidioides* sp. fungus in a bodily fluid such as blood are provided.

2 Claims, 9 Drawing Sheets

Sero-positive Dogs

| Dog Name | Titer | Peptide 1 MS Peak Area |
|---|---|---|
| Bentley | IgG 1:4 | 6678 |
| Bily | IgG/M 1:32 | 973 |
| Gizmo | IgG 1:2 (weak) | 7464 |
| Joy | IgG 1:32 | 3749 |
| Lexie | IgG/M 1:32 | 6780 |
| Maui | IgG/M 1:128 | 8120 |
| Riley | IgG 1:8 | 4454 |
| Rugby | IgG 1:2 (weak) | 2004 |
| Tyas | IgG/M 1:32 | 7544 |

Sero-negative Dogs

| Dog Name | Titer | Peptide 1 MS Peak Area |
|---|---|---|
| Chloe | sero-negative | 0 |
| Cooper | sero-negative | 1121 |
| Heidi | sero-negative | 0 |
| Hilo | sero-negative | 0 |
| Lola* | sero-negative | 0 |
| Jasmine | sero-negative | 6357 |
| Nina | sero-negative | 1618 |
| Sierra | sero-negative | 3874 |
| Sophie | sero-negative | 0 |
| Zoe | sero-negative | 0 |

*Maintenance on Fluconazole

Peptides from Cocci and Human proteins were detected by LC-MS/MS in plasma

| Cocci Proteins | | Human wild-type proteins |
|---|---|---|
| CPSG_08281 | hypothetical protein | Complement C4-A |
| CPSG_07785 | ubiquitin conjugation factor E4 | Apolipoprotein A-IV |
| CPSG_09853 | predicted protein | Fibrinogen alpha chain |
| CPSG_06055 | nucleolar GTP-binding protein 1 | Complement C3 |
| CPSG_06793 | conserved hypothetical protein | Hemoglobin subunit beta |
| CPSG_08637 | hypothetical protein | Alpha-2-antiplasmin |
| CPSG_05011 | conserved hypothetical protein | Serum amyloid A protein |
| CPSG_00417 | hypothetical protein | Alpha-1-antichymotrypsin |
| CPSG_09060 | predicted protein | Fibrinogen beta chain |
| CPSG_05809 | predicted protein | Inter-alpha-trypsin inhibitor heavy chain |
| CPSG_07446 | pH-response transcription factor pacC/RIM10 | Apolipoprotein E |
| CPSG_04225 | conserved hypothetical protein | Hemoglobin subunit alpha |
| CPSG_03280 | bromodomain-containing protein | Kininogen-1 |
| CPSG_06595 | conserved hypothetical protein | Thymosin beta-4-like protein 1 |
| CPSG_01243 | conserved hypothetical protein | Sodium channel and clathrin linker 1 |
| | | Anosmin-1 |

LC-MS/MS Detection of coccidioidal peptide in plasma by Multiple Reaction Monitoring

| | Patient ID | Titer | PGLD peptide (~pg/µl) |
|---|---|---|---|
| Active Disease | 1-0001 | 1:8 | 57.3 |
| | 1-0003 | 1:8 | 89.1 |
| | 1-0006 | 1:32 | 78.4 |
| | 1-0009 | 1:16 | 46.9 |
| | 1-0013 | 1:02 | 73.2 |
| Healthy non-immune | 2-0002 | ND | 0 |
| | 2-0005 | ND | 0 |
| | 2-0006 | ND | 0 |
| | 2-0007 | ND | 0 |
| | 2-0009 | ND | 0 |
| Healthy immune | 3-0001 | NA | 0 |
| | 3-0002 | NA | 0 |
| | 3-0004* | Negative | 0 |
| | 3-0005 | Neg in 2007 | 47.3 |
| | 3-0006 | 1:32 | 0 |

*400mg fluconazole per day

SEQUENCE LISTING

<160> NUMBER OF SEQ ID NOS: 4

<210> SEQ ID NO 1
<211> LENGTH: 9
<212> TYPE: PRT
<213> ORGANISM: Coccidioides posadasii

<400> SEQUENCE: 1

Phe Asp Thr Thr Ile Gly Glu Lys Leu
1               5

<210> SEQ ID NO 2
<211> LENGTH: 579
<212> TYPE: PRT
<213> ORGANISM: Coccidioides posadasii

<400> SEQUENCE: 2

Met Ala Pro Pro Leu Leu Asn Ser Ser Asn Ser Phe Asp Ala Lys Lys
1               5                   10                  15

Pro Val Thr Tyr Ser Thr Thr Ala Leu Lys Arg Trp Ser Cys Leu Asn
                20                  25                  30

Asn Asn Lys Asp Leu Pro Ala Ile Pro Asp Val Lys Ala Ile His Val
            35                  40                  45

```
Tyr Asp Phe Asp Asn Thr Leu Phe Asn Ser Pro Leu Pro Asn Pro Gln
 50                  55                  60

Leu Trp Asn Gly Leu Thr Ile Gly Phe Leu Gln Ala Tyr Glu Ser Phe
 65                  70                  75                  80

Ala Asn Gly Gly Trp Trp His Asp Pro Asn Ile Leu Ala Ala Thr Gly
                 85                  90                  95

Gln Gly Ile Asp Val Glu Glu Pro Leu Ala Trp Lys Gly Trp Trp Asn
            100                 105                 110

Glu Gln Ile Val Glu Leu Val Glu Leu Ser Met Lys Gln Lys Asp Val
            115                 120                 125

Leu Thr Val Leu Leu Thr Gly Arg Ala Glu Ser Phe Ala Glu Ile
        130                 135                 140

Ile Lys Arg Ile Val Lys Ser Arg Ser Leu Glu Phe Asp Leu Val Cys
145                 150                 155                 160

Leu Lys Pro Glu Ile Gly Pro Asn Ser Gln Arg Phe Ser Ser Thr Ile
                165                 170                 175

Asn Phe Lys Gln Ile Phe Leu Glu Asp Met Ile Phe Thr Tyr Lys His
            180                 185                 190

Ala Asp Glu Ile Arg Val Tyr Glu Asp Arg Ile Arg His Val Lys Gly
        195                 200                 205

Phe Arg Asp Tyr Phe Glu Gln Phe Asn Leu Gln Phe Leu Ala Pro Asn
210                 215                 220

Ser His Pro Ile Arg Lys Ser Ile Thr Ala Glu Val Ile His Val Ala
225                 230                 235                 240

Glu Ser Thr Arg Tyr Leu Pro Pro Val Ala Glu Ala Ala Glu Val Gln
                245                 250                 255

Arg Met Ile Asn Ser His Asn Ala Ile Val Thr Ala Ala Ser Gly Asn
            260                 265                 270

Val Thr Lys Ser Pro Tyr Gly Arg Leu Arg Ile His Arg Val Ile Phe
        275                 280                 285

Tyr Thr Gly Tyr Met Leu Asp Asn Ala Asp Ser Glu Arg Leu Val Lys
290                 295                 300

Tyr Leu Thr Leu Pro Met Leu Ser Pro Ser Leu Val Asp Ser Gly Asp
305                 310                 315                 320

Val Lys Leu Met Ala Asn Thr Ile Leu Ile Thr Pro Arg Ala Ala Pro
                325                 330                 335

Lys Ala Ile Leu Asp Arg Val Gly Gly Ile Gly Lys Val Val Arg Trp
            340                 345                 350

Arg Val Thr Asp Thr Ala Val Phe Glu Asn Lys Ile Trp Ala Ala Arg
        355                 360                 365

Val Ala Pro Ile Ser Asp Ser Glu Asp Ile Tyr Thr Asp Asn Pro Asp
370                 375                 380

Pro Val Val Leu Ala Leu Arg Arg Gly Ala Arg Pro Ile Asp Val
385                 390                 395                 400

Gly Arg Ile Arg Asn Trp Asn Pro Val Ser Glu Asn Ala Leu Val
                405                 410                 415

Phe Asp Thr Thr Ile Gly Glu Lys Leu Val Leu Arg Val Ala Glu Asp
            420                 425                 430

Asn Ser Asp Asp Gly Asp Gly Glu Ala Pro Asn Val Gly Arg Pro Phe
        435                 440                 445

Lys Arg Arg His Lys Tyr Asp Thr Arg Asp Asn Glu Asp Val Pro Ser
450                 455                 460
```

```
Tyr Pro Lys Glu Asn His Arg Glu Pro Gly Arg Pro Arg Gly Gly Tyr
465                 470                 475                 480

Asn Asp Tyr Ser Arg Ser Arg His Glu Arg His Pro Asp Asp Arg Pro
            485                 490                 495

Pro Arg His Tyr His Asp Glu Asp Ser Arg Arg Gly Pro Pro Pro Pro
                500                 505                 510

Gly Tyr Arg Gly Gly Arg Gly Arg Ala Gly Arg Gly Gly Arg Gly
            515                 520                 525

Gly Arg Gly Arg Gly Arg Ala Pro Gly Pro Arg Glu Gly Gly Tyr
530                 535                 540

Ala Gly Tyr Arg Ser Leu Asp Asp Tyr Pro Ser Ser Arg Pro Gly Tyr
545                 550                 555                 560

Asp Gly Ala Gly Asp Asp Arg Gly Gly Pro Gly Ser Gly Asn Pro Val
            565                 570                 575

Met Asn Tyr

<210> SEQ ID NO 3
<211> LENGTH: 596
<212> TYPE: PRT
<213> ORGANISM: Coccidioides immitis

<400> SEQUENCE: 3

Met Leu Arg Ser Gly Lys His Ile Ser Ala Arg Ala Ala Leu Tyr Ser
1               5                   10                  15

Lys Met Ala Pro Pro Leu Leu Asn Ser Ser Asn Ser Phe Asp Ala Lys
            20                  25                  30

Lys Pro Val Thr Tyr Ser Thr Thr Ala Leu Lys Arg Trp Ser Cys Leu
            35                  40                  45

Asn Asn Asn Lys Asp Leu Pro Ala Ile Pro Asp Val Lys Ala Ile His
50                  55                  60

Val Tyr Asp Phe Asp Asn Thr Leu Phe Asn Ser Pro Leu Pro Asn Pro
65                  70                  75                  80

Gln Leu Trp Asn Gly Leu Thr Ile Gly Phe Leu Gln Ala Tyr Glu Ser
            85                  90                  95

Phe Ala Asn Gly Gly Trp Trp His Asp Pro Asn Ile Leu Ala Ala Thr
                100                 105                 110

Gly Gln Gly Ile Asp Val Glu Glu Pro Leu Ala Trp Lys Gly Trp Trp
            115                 120                 125

Asn Glu Gln Ile Val Glu Leu Val Glu Leu Ser Met Lys Gln Lys Asp
130                 135                 140

Val Leu Thr Val Leu Leu Thr Gly Arg Ala Glu Ser Ser Phe Ala Glu
145                 150                 155                 160

Ile Ile Lys Arg Ile Val Lys Ser Arg Ser Leu Glu Phe Asp Leu Val
            165                 170                 175

Cys Leu Lys Pro Glu Ile Gly Pro Asn Ser Gln Arg Phe Ser Ser Thr
            180                 185                 190

Ile Asn Phe Lys Gln Ile Phe Leu Glu Asp Met Ile Phe Thr Tyr Lys
            195                 200                 205

His Ala Asp Glu Ile Arg Val Tyr Glu Asp Arg Ile Arg His Val Lys
210                 215                 220

Gly Phe Arg Asp Tyr Phe Glu Gln Phe Asn Leu Gln Phe Leu Ala Pro
225                 230                 235                 240

Asn Ser His Pro Ile Arg Lys Ser Ile Thr Ala Glu Val Ile His Val
            245                 250                 255
```

```
Ala Glu Ser Thr Arg Tyr Leu Pro Pro Val Ala Glu Ala Glu Val
            260                 265                 270

Gln Arg Met Ile Asn Ser His Asn Ala Ile Val Thr Ala Ala Ser Gly
        275                 280                 285

Asn Val Thr Lys Ser Pro Tyr Gly Arg Leu Arg Ile His Arg Val Ile
        290                 295                 300

Phe Tyr Thr Gly Tyr Met Leu Ala Asn Ala Asp Ser Glu Arg Leu Val
305                 310                 315                 320

Lys Tyr Leu Thr Leu Pro Met Ile Ser Pro Ser Leu Val Asp Ser Gly
                325                 330                 335

Asp Val Lys Leu Met Ala Asn Thr Ile Leu Ile Thr Pro Arg Ala Ala
            340                 345                 350

Pro Lys Ala Ile Leu Asp Arg Val Gly Gly Ile Gly Lys Val Val Arg
        355                 360                 365

Trp Arg Val Thr Asp Thr Ala Val Phe Glu Asn Lys Ile Trp Ala Ala
        370                 375                 380

Arg Val Ala Pro Ile Ser Asp Ser Glu Asp Ile Tyr Thr Asp Asn Pro
385                 390                 395                 400

Asp Pro Val Val Val Leu Ala Leu Arg Arg Gly Ala Arg Pro Ile Asp
                405                 410                 415

Val Gly Arg Ile Arg Asn Trp Asn Pro Val Ser Glu Glu Asn Ala Leu
            420                 425                 430

Val Phe Asp Thr Thr Ile Gly Glu Lys Leu Val Leu Arg Val Ala Glu
        435                 440                 445

Asp Asn Ser Asp Asp Gly Asp Gly Glu Ala Pro Asn Val Gly Arg Pro
        450                 455                 460

Phe Lys Arg Arg His Lys Tyr Asp Thr Arg Asp Asn Glu Asp Val Pro
465                 470                 475                 480

Ser Tyr Pro Lys Glu Asn His Arg Glu Pro Gly Arg Pro Gly Gly
                485                 490                 495

Tyr Asn Asp Tyr Ser Arg Ser Arg His Glu Arg His Pro Asp Asp Arg
                500                 505                 510

Pro Pro Arg His Tyr His Asp Glu Asp Ser Arg Arg Gly Pro Pro Pro
            515                 520                 525

Pro Gly Tyr Arg Gly Gly Arg Gly Arg Ala Gly Arg Gly Gly Arg
        530                 535                 540

Gly Gly Arg Gly Arg Gly Arg Ala Pro Gly Pro Arg Glu Gly Gly
545                 550                 555                 560

Tyr Ala Gly Tyr Arg Ser Leu Asp Asp Tyr Pro Ser Ser Arg Pro Gly
                565                 570                 575

Tyr Asp Gly Ala Gly Asp Asp Arg Gly Gly Pro Gly Ser Gly Asn Pro
            580                 585                 590

Val Met Asn Tyr
        595

<210> SEQ ID NO 4
<211> LENGTH: 15
<212> TYPE: PRT
<213> ORGANISM: yeast

<400> SEQUENCE: 4

Pro Gly Leu Asp Ser Lys Ser Leu Ala Cys Thr Phe Ser Gln Val
1               5                   10                  15
```

METHODS OF DETECTION OF *COCCIDIOIDES* SPECIES IN BODILY FLUID

CROSS-REFERENCE TO RELATED APPLICATIONS

This application claims the benefit of U.S. provisional Application No. 61/532,936 filed on Sep. 9, 2011, which is incorporated by reference herein in its entirety.

BACKGROUND OF THE INVENTION

Coccidioidomycosis or "Valley Fever" (VF) is caused by the fungus *Coccidioides* sp., which lives in soils of the southwestern US and San Juaquin Valley Calif. When soil is disturbed, humans and animals can inhale fungal spores that germinate in the lung to produce a respiratory infection that ranges in severity from mild to life threatening. An estimated 150,000 infections occur annually, and about 60% occur in Arizona. In Arizona in 2009 over 300,000 tests for Valley Fever were ordered by physicians. Coccidioidomycosis is a respiratory illness that is acquired through inhalation of airborne arthroconidia (spores), and produces a spectrum of illness, ranging from mild to severe and life-threatening pulmonary illness. Maricopa County has been the epicenter of a coccidioidal epidemic for years, with the incidence rising nearly six-fold since 1993.

Coccidioidomycosis in humans and dogs is difficult to diagnose and is often misdiagnosed as bacterial or viral community acquired pneumonia in humans. If a patient is suspected of having VF, serologic testing is performed, i.e. serum is tested for the presence of antibodies to coccidioidal antigens. Currently available tests to distinguish VF from other community acquired pneumoniae are based on the ability of patients to mount an antibody response to the fungus. Unfortunately, the antibody-based tests are inadequate for many patients because it may take weeks to months to develop such an antibody response (leading to delayed diagnosis), and many immunocompromised patients are unable to mount any antibody response at all. The problem is that even if a patient does not possess antibodies against the fungus, he/she may still have the disease. It may then become necessary to perform an invasive procedure such as bronchoalveolar lavage or biopsy of lung or other infected tissues to determine by culture or by direct histopathological exam if the fungus is present. Such procedures are expensive and put the patient at risk for procedure-related complications. Therefore a blood or other bodily fluid test to detect coccidioidal proteins would allow a more definitive diagnosis to be made even if a subject's serology is negative.

DETAILED DESCRIPTION OF THE INVENTION

In a first aspect, the present invention provides methods for diagnosing Coccidioidomycosis comprising testing a fluid sample selected from the group consisting of blood, urine, saliva, and or bronchoalveolar lavage fluid (BAL) obtained from a subject at risk of Coccidioidomycosis for presence of detectable levels of expression of a polypeptide comprising the amino acid sequence FDTTIGEKL (SEQ ID NO. 1), wherein the presence of detectable levels of expression of the polypeptide indicate that the subject has Coccidioidomycosis.

In this first aspect, detecting the recited fungal peptide in the body fluid, such as in circulation, instead of relying on the host to make antibodies against the fungus, provides a more definitive diagnosis of infection. This allows physicians or veterinarians to rule in *Coccidioides* sp. as the etiologic agent of the symptoms exhibited by the subject.

In one preferred embodiment of this first aspect, the methods comprise (a) contacting the fluid sample from a subject at risk of Coccidioidomycosis with an antibody selective for a polypeptide comprising the amino acid sequence FDTTIGEKL (SEQ ID NO. 1), under conditions to promote antibody binding to its selective antigen;

(b) removing unbound antibodies; and (c) detecting antibody-antigen complexes, wherein the presence of detectable levels of the antibody-antigen complexes indicate that the subject has Coccidioidomycosis In a second aspect, the invention provides methods for monitoring treatment of Coccidioidomycosis, comprising testing a fluid sample selected from the group consisting of blood, urine, saliva, and or bronchoalveolar lavage fluid (BAL) from a subject being treated for Coccidioidomycosis for presence of detectable levels of expression of a polypeptide comprising the amino acid sequence FDTTIGEKL (SEQ ID NO. 1), wherein the presence of detectable levels of expression of the polypeptide indicate that the subject's treatment should be continued.

In one preferred embodiment of this second aspect, the methods comprise (a) contacting the fluid sample from a subject being treated for Coccidioidomycosis with an antibody selective for a polypeptide comprising the amino acid sequence FDTTIGEKL (SEQ ID NO. 1), under conditions to promote antibody binding to its selective antigen;

(b) removing unbound antibodies; and (c) detecting antibody-antigen complexes, wherein the presence of detectable levels of the antibody-antigen complexes indicate that the subject's treatment should be continued.

In the second aspect of the invention, the methods are used to monitor subjects for decreases in fungal burden (fungemia) and provide valuable information to an attending physician in determining when to stop anti-fungal chemotherapy. Current treatments for coccidioidomycosis include Fluconazole, Amphotericin B, itraconazole or ketoconazole, posaconazole and voriconazole. The presence of the recited antigen or antibodies to the antigen, in fluid sample indicates that the *Coccidioides* sp. infection has not cleared, and thus Coccidioidomycosis is either still present or can easily re-emerge.

As used herein, "Coccidioidomycosis" (also known as "California disease "Desert rheumatism," "San Joaquin valley fever," and "Valley fever) is a fungal disease caused by infection with *Coccidioides immitis* or *C. posadasii* (collectively "*Coccidioides* sp."). Subjects with Coccidioidomycosis present with one or more symptoms listed below:

Blood-tinged sputum
Chest pain (can vary from a mild sense of constriction to severe pain, may get worse when taking a deep breath)
Chills
Cough
Lung abscess
Fever
Headache
Joint stiffness
Loss of appetite
Muscle aches
Muscle stiffness
Neck stiffness or shoulder stiffness
Night sweats
Rash, may be painful, red nodules on lower legs
Skin lesions
Sensitivity to light
Sweating, excessive
Weight loss
Wheezing
Ankle, feet, and leg swelling
Arthritis
Enlarged or draining lymph nodes
Joint pain
Joint swelling As used herein, "at risk of Coccidioidomycosis" means that the subject is suffering from one or more symptoms of Coccidioidomycosis, but has not been diagnosed with Coccidioidomycosis. Such symptoms include, but are not limited to those listed above.

For purposes of the present invention, Coccidioidomycosis includes primary pulmonary coccidioidomycosis (spore inhalation leading), disseminated coccidioidomycosis (systemic infection in which 15-20% of subjects develop skin lesions), and primary cutaneous coccidioidomycosis (skin condition caused by infection). In disseminated disease, infection may spread to the bones, lungs, liver, lining covering the brain and spinal cord (meninges), brain, skin, heart, and the sac around the heart (pericardium). Meningitis occurs in 30-50% of cases of disseminated disease. The disease may get worse quickly in immunosuppressed subjects.

For purposes of the present invention, Coccidioidomycosis includes both acute and chronic disease.

In a preferred embodiment, those subjects at risk of Coccidioidomycosis live in or have vistited Arizona, California, Nevada, New Mexico, Texas, Utah, South America, and/or Central America (including but not limited to Mexico) or have come into contact with materials potentially contaminated with dust or soil from those areas. Such materials may be any fomite (ie: any inanimate object or substance capable of carrying infectious organisms) exposed to the outdoor environment in an endemic area, and include, but are not limited to, automobiles and automobile components (such as tires) and fruit.

Coccidioidomycosis infections can occur in subjects including, but not limited to, humans, dogs, cattle, deer, elk, fish, mules, livestock, apes, kangaroos, wallabies, tigers, bears, badgers, otters and marine mammals. In a preferred embodiment of any aspect of the invention, the subject is a human or dog.

As used herein, a "polypeptide comprising the amino acid sequence FDTTIGEKL (SEQ ID NO. 1)" includes any polypeptides that include the recited peptide. In one preferred embodiment, the polypeptide is as follows:

```
hypothetical protein CPC735_066600
[Coccidioides posadasii C735 delta SOWgp]",
Genbank accession number EER25560.1
(SEQ ID NO. 2):
  1 mappllnssn sfdakkpvty sttalkrwsc lnnnkdlpai
    pdvkaihvyd fdntlfnspl 61 pnpqlwnglt igflqayesf anggwwhdpn ilaatgqgid
    veeplawkgw wneqivelve 121 lsmkqkdvlt vlltgraess faeiikrivk srslefdlvc
    lkpeigpnsq rfsstinfkq 181 ifledmifty khadeirvye drirhvkgfr dyfeqfnlqf
    lapnshpirk sitaevihva 241 estrylppva eaaevqrmin shnaivtaas gnvtkspygr
    lrihrvifyt gymldnadse 301 rlvkyltlpm lspslvdsgd vklmantili tpraapkail
    drvggigkvv rwrvtdtavf 361 enkiwaarva pisdsediyt dnpdpvvvla lrrgarpidv
    grirnwnpvs eenalvfdtt 421 igeklvlrva ednsddgdge apnvgrpfkr rhkydtrdne
    dvpsypkenh repgrprggy 481 ndysrsrher hpddrpprhy hdedsrrgpp ppgyrgggrg
    ragrggrggr grgrapgpre 541 gggyagyrsl ddypssrpgy dgagddrggp gsgnpvmny hypothetical protein CIMG_05522
[Coccidioides immitis RS] NCBI
Reference Sequence XP_001246081.1
(SEQ ID NO. 3):
  1 mlrsgkhisa raalyskmap pllnssnsfd akkpvtystt
    alkrwsclnn nkdlpaipdv 61 kaihvydfdn tlfnsplpnp qlwngltigf lqayesfang
    gwwhdpnila atgqgidvee 121 plawkgwwne qivelvelsm kqkdvltvll tgraessfae
    iikrivksrs lefdlvclkp 181 eigpnsqrfs stinfkqifl edmiftykha deirvyedri
    rhvkgfrdyf eqfnlqflap 241 nshpirksit aevihvaest rylppvaeaa evqrminshn
    aivtaasgnv tkspygrlri 301 hrvifytgym lanadserlv kyltlpmisp slvdsgdvkl
    mantilitpr aapkaildrv 361 ggigkvvrwr vtdtavfenk iwaarvapis dsediytdnp
    dpvvvlalrr garpidvgri 421 rnwnpvseen alvfdttige klvlrvaedn sddgdgeapn
    vgrpfkrrhk ydtrdnedvp 481 sypkenhrep grprggyndy srsrherhpd drpprhyhde
    dsrrgppppg yrgggrgrag 541 rggrggrgrg rapgpreggg yagyrslddy pssrpgydga
    gddrggpgsg npvmny
```

In a further preferred embodiment of all aspects and embodiments of the invention, the polypeptide is 3 kD or less. In a further preferred embodiment, the polypeptide consists of the peptide FDTTIGEKL (SEQ ID NO. 1). The peptide sequence is found in both strains, *C. immitis* and *C. posadasii*. There is no difference in clinical symptoms based on the strain with which one is infected.

In a preferred embodiment of all aspects and embodiments of the invention, the fluid sample is a blood sample. Any suitable blood sample obtained from the subject may be used, including but not limited to whole blood and blood plasma. In a preferred embodiment, a blood plasma sample is used. Methods for preparing blood plasma are well known in the art; such methods include those described below. In one embodiment, plasma is prepared by centrifuging a blood sample under conditions suitable for pelleting of the cellular component of the blood.

In one preferred embodiment of all aspects and embodiments of the invention, the methods comprise analyzing a blood plasma sample of the subject for FDTTIGEKL (SEQ ID NO. 1) or FDTTIGEKL (SEQ ID NO. 1)-containing peptides of 3 kD or less; in a further preferred embodiment, the method comprises isolating FDTTIGEKL (SEQ ID NO. 1) or FDTTIGEKL (SEQ ID NO. 1)-containing peptides of 3 kD or less from the blood plasma sample. In another preferred embodiment, the analyzing comprises a technique selected from the group consisting of mass spectrometry (MS), two dimensional gel electrophoresis, Western blotting, immunofluorescence, ELISAs, antigen capture assays (including dipstick antigen capture assays) and mass spec immunoAssay (MSIA). In one exemplary preferred embodiment, the methods comprise MS analysis to detect FDTTIGEKL (SEQ ID NO. 1) or FDTTIGEKL (SEQ ID NO. 1)-containing peptides of 3 kD or less, in which HPLC is used to separate plasma peptides. In this embodiment, it is further preferred that a dual MS profile is generated, with a first MS to provide a mass of the protein fragments present in the plasma sample, and a second MS to provide the sequence of the peptides based on, for example, ion fragmentation spectra.

In a further preferred embodiment of all aspects of the invention, the methods comprise ELISA detection assays or antigen capture assays (including dipstick antigen capture assays). In a further preferred embodiment, detecting expression of the peptide comprises detecting messenger RNA by PCR. While this is an indirect measure of peptide expression, since the protein is expressed, a transcript encoding the peptide can be detected as well. In one non-limiting preferred embodiment, the methods comprise competitive ELISA, wherein following incubation of the blood sample with the antibody selective for a polypeptide comprising the amino acid sequence FDTTIGEKL (SEQ ID NO. 1), under conditions to promote antibody binding to its selective antigen, the mixture is added to ELISA plates pre-coated with streptavidin-biotin-FDTTIGEKL (SEQ ID NO. 1) and further incubated under similar binding conditions for a desired period of time. Subsequently, the plates are washed free of unbound antibody-peptide followed by addition of a pre-determined dilution of a detection reagent, permitting the concentration of FDTTIGEKL (SEQ ID NO. 1)-containing peptides in the blood sample to be calculated. In another preferred embodiment, antigen capture ELISAs are carried out, wherein antibodies are coated onto the ELISA plate, the fluid/blood sample is contacted with the ELISA plate under suitable conditions, unbound sample is removed by washing, and detection is carried out.

In a third aspect, the present invention provides methods for diagnosing *Coccidioides* sp. infection (which may be symptomatic or asymptomatic) comprising testing a fluid sample obtained from a subject at risk of having been infected with *Coccidioides* sp. for presence of detectable levels of a polypeptide comprising the amino acid sequence FDTTIGEKL (SEQ ID NO. 1), wherein the presence of detectable levels of the polypeptide indicate that the subject has been infected with *Coccidioides* sp.

In this third aspect, detecting the recited fungal peptide in the fluid sample instead of relying on the host to make antibodies against the fungus, provides a definitive diagnosis of infection, and that the subject may be at risk of developing Coccidioidomycosis. The methods would be useful, for example, in testing of non-symptomatic subjects in regions where *Coccidioides* sp. infection is endemic (ie: Arizona, California, Nevada, New Mexico, Texas, Utah, South America, and/or Central America (including but not limited to Mexico)), or for non-symptomatic subjects that have come into contact with materials potentially contaminated with dust or soil from those areas.

In one preferred embodiment of this third aspect, the methods comprise (a) contacting a blood sample from a subject at risk of *Coccidioides* sp. with an antibody selective for a polypeptide comprising the amino acid sequence FDTTIGEKL (SEQ ID NO. 1), under conditions to promote antibody binding to its selective antigen;

(b) removing unbound antibodies; and (c) detecting antibody-antigen complexes, wherein the presence of detectable levels of the antibody-antigen complexes indicate that the subject has been infected with *Coccidioides* sp.

In a fourth aspect, the present invention provides isolated peptides consisting of the amino acid sequence FDTTIGEKL (SEQ ID NO. 1). The peptides of the invention can be used, for example, to produce antibodies for use in the methods of the present invention. The isolated peptides of the invention may be recombinantly produced or chemically synthesized. Preferably, the peptides of the present invention are chemically synthesized. Synthetic polypeptides, prepared using the well known techniques of solid phase, liquid phase, or peptide condensation techniques, or any combination thereof, can include natural and unnatural amino acids. Amino acids used for peptide synthesis may be standard Boc (Na-amino protected Na-t-butyloxycarbonyl)amino acid resin with the standard deprotecting, neutralization, coupling and wash protocols of the original solid phase procedure of Merrifield (1963, J. Am. Chem. Soc. 85:2149-2154), or the base-labile Na-amino protected 9-fluorenylmethoxycarbonyl (Fmoc) amino acids first described by Carpino and Han (1972, J. Org. Chem. 37:3403-3409). Both Fmoc and Boc Na-amino protected amino acids can be obtained from Sigma, Cambridge Research Biochemical, or other chemical companies familiar to those skilled in the art. In addition, the peptides can be synthesized with other Na-protecting groups that are familiar to those skilled in this art. Solid phase peptide synthesis may be accomplished by techniques familiar to those in the art, or using automated synthesizers. The peptides of the invention may comprise L-amino acids, D-amino acids (which are resistant to L-amino acid-specific proteases in vivo), or a combination of D- and L-amino acids to convey special properties. In addition, the polypeptides can have peptidomimetic bonds, such as ester bonds, to prepare peptides with novel properties. For example, a peptide may be generated that incorporates a reduced peptide bond, i.e., $R_1$—$CH_2$—NH—$R_2$, where $R_1$ and $R_2$ are amino acid residues or sequences. A reduced peptide bond may be introduced as a dipeptide subunit. Such a peptide would be resistant to protease activity, and would possess an extended half-live in vivo. The isolated peptides may be further modified with other groups as desired to provide special properties, such as linkage to polyethylene glycol to increase plasma half-life for therapeutic use.

The peptides may be subjected to conventional pharmaceutical operations such as sterilization and/or may contain conventional adjuvants, such as preservatives, stabilizers, wetting agents, emulsifiers, buffers, adjuvants, etc., prior to being disposed on the heparin coating. The peptides may be dissolved in saline, water, polyethylene glycol, propylene glycol, carboxymethyl cellulose colloidal solutions, ethanol, corn oil, peanut oil, cottonseed oil, sesame oil, tragacanth gum, and/or various buffers, or may be admixed with lactose, sucrose, starch powder, cellulose esters of alkanoic acids, stearic acid, talc, magnesium stearate, magnesium oxide, sodium and calcium salts of phosphoric and sulphuric acids, acacia, gelatin, sodium alginate, polyvinylpyrrolidine, dextran sulfate, heparin-containing gels, and/or polyvinyl alcohol prior to being disposed on the heparin coating.

In a fifth aspect, the present invention provides substantially purified nucleic acids encoding a peptide of the present invention. The substantially purified nucleic acid sequence may comprise RNA or DNA. Such nucleic acids are useful, for example, for preparing recombinant expression vectors to make large amounts of the peptides of the invention. As used herein, "substantially purified nucleic acids" are those that have been removed from their normal surrounding nucleic acid sequences in the genome or in cDNA sequences. Such substantially purified nucleic acid sequences may comprise additional sequences useful for promoting expression and/or purification of the encoded protein, including but not limited to polyA sequences, modified Kozak sequences, and sequences encoding epitope tags, export signals, and secretory signals, nuclear localization signals, and plasma membrane localization signals. In one preferred embodiment, the substantially purified nucleic acid coding region consists of a nucleic acid of encoding a peptide of the invention.

In a sixth aspect, the present invention provides recombinant expression vectors comprising the substantially purified nucleic acid of the invention operatively linked to a promoter. Such recombinant expression vectors are useful, for example, for generating host cells that produce large amounts of the peptides of the invention. "Recombinant expression vector" includes vectors that operatively link a nucleic acid coding region or gene to any promoter capable of effecting expression of the gene product. The promoter sequence used to drive expression of the disclosed nucleic acid sequences in a mammalian system may be constitutive (driven by any of a variety of promoters, including but not limited to, CMV, SV40, RSV, actin, EF) or inducible (driven by any of a number of inducible promoters including, but not limited to, tetracycline, ecdysone, steroid-responsive). The construction of expression vectors for use in transfecting prokaryotic cells is also well known in the art, and thus can be accomplished via standard techniques. (See, for example, Sambrook, Fritsch, and Maniatis, in: Molecular Cloning, A Laboratory Manual, Cold Spring Harbor Laboratory Press, 1989; *Gene Transfer and Expression Protocols*, pp. 109-128, ed. E. J. Murray, The Humana Press Inc., Clifton, N.J.), and the Ambion 1998 Catalog (Ambion, Austin, Tex.). The expression vector must be replicable in the host organisms either as an episome or by integration into host chromosomal DNA. In a preferred embodiment, the expression vector comprises a plasmid. However, the invention is intended to include other expression vectors that serve equivalent functions, such as viral vectors.

In a seventh aspect, the present invention provides host cells that have been transfected with the recombinant expression vectors disclosed herein, wherein the host cells can be either prokaryotic or eukaryotic. The cells can be transiently or stably transfected. Such transfection of expression vectors into prokaryotic and eukaryotic cells can be accomplished via any technique known in the art, including but not limited to standard bacterial transformations, calcium phosphate co-precipitation, electroporation, or liposome mediated-, DEAE dextran mediated-, polycationic mediated-, or viral mediated transfection. (See, for example, *Molecular Cloning: A Laboratory Manual* (Sambrook, et al., 1989, Cold Spring Harbor Laboratory Press; *Culture of Animal Cells: A Manual of Basic Technique*, 2nd Ed. (R. I. Freshney. 1987. Liss, Inc. New York, N.Y.).

In an eighth aspect, the present invention provides isolated ligands, wherein the ligand selectively binds to the peptide FDTTIGEKL (SEQ ID NO. 1). The ligands of the invention can be used, for example, in the methods of the invention disclosed herein. In one preferred embodiment, the ligand is selected from the group consisting on antibodies, antibody fragments, and aptamers. It is well within the level of those of skill in the art to make antibodies and aptamers to the recited peptide. Such antibodies or aptamers are those that selectively bind to the peptide of interest, as defined above. In a preferred embodiment, the ligand is an antibody. Suitable antibodies include, but are not limited to, polyclonal, monoclonal, and humanized monoclonal antibodies.

As used in this application, "isolated" means that the "isolated peptide" or "isolated ligand" has been separated from its in vivo cellular environment, and constitutes at least 90% of the peptide/ligand component present in the isolated sample; preferably at least 91%, 92%, 93%, 94%, 95%, 96%, 97%, 98%, 99%, or more of the peptide/ligand component present in the isolated sample. It is further preferred that the isolated peptide or ligand is substantially free of gel agents, such as polyacrylamide, agarose, and chromatography reagents.

As used herein, "selectively bind" means preferential binding of the ligand to FDTTIGEKL (SEQ ID NO. 1), as opposed to one or more other biological molecules, structures, cells, tissues, etc., as is well understood by those of skill in the art.

Antibodies can be made by well-known methods, such as described in Harlow and Lane, Antibodies; A Laboratory Manual, Cold Spring Harbor Laboratory, Cold Spring Harbor, N.Y., (1988). In one example, preimmune serum is collected prior to the first immunization. The substantially purified peptide of the invention, or a fragment thereof, together with an appropriate adjuvant, is injected into an animal in an amount and at intervals sufficient to elicit an immune response. Animals are bled at regular intervals, preferably weekly, to determine antibody titer. The animals may or may not receive booster injections following the initial immunization. At about 7 days after each booster immunization, or about weekly after a single immunization, the animals are bled, the serum collected, and aliquots are stored at about −20° C. Polyclonal antibodies against the proteins and peptides of the invention can then be purified directly by passing serum collected from the animal through a column to which non-antigen-related proteins prepared from the same expression system are bound.

Monoclonal antibodies can be produced by obtaining spleen cells from the animal. (See Kohler and Milstein, Nature 256, 495-497 (1975)). In one example, monoclonal antibodies (mAb) of interest are prepared by immunizing inbred mice with a peptide of the invention, or an antigenic fragment thereof. The mice are immunized by the IP or SC route in an amount and at intervals sufficient to elicit an immune response. The mice receive an initial immunization on day 0 and are rested for about 3 to about 30 weeks. Immunized mice are given one or more booster immunizations of by the intravenous (IV) route. Lymphocytes, from antibody positive mice are obtained by removing spleens from immunized mice by standard procedures known in the art. Hybridoma cells are produced by mixing the splenic lymphocytes with an appropriate fusion partner under conditions which will allow the formation of stable hybridomas. The antibody producing cells and fusion partner cells are fused in polyethylene glycol at concentrations from about 30% to about 50%. Fused hybridoma cells are selected by growth in hypoxanthine, thymidine and aminopterin supplemented Dulbecco's Modified Eagles Medium (DMEM) by procedures known in the art. Supernatant fluids are collected from growth positive wells and are screened for antibody production by an immunoassay such as solid phase immunoradioassay. Hybridoma cells from antibody positive wells are cloned by a technique such as the soft agar technique of MacPherson, Soft Agar Techniques, in Tissue Culture Methods and Applications, Kruse and Paterson, Eds., Academic Press, 1973.

"Humanized antibody" refers to antibodies derived from a non-human antibody, such as a mouse monoclonal antibody. Alternatively, humanized antibodies can be derived from chimeric antibodies that retains or substantially retains the antigen-binding properties of the parental, non-human, antibody but which exhibits diminished immunogenicity as compared to the parental antibody when administered to humans. For example, chimeric antibodies can comprise human and murine antibody fragments, generally human constant and mouse variable regions. Humanized antibodies can be prepared using a variety of methods known in the art, including but not limited to (1) grafting complementarity determining regions from a non-human monoclonal antibody onto a human framework and constant region ("humanizing"), and (2) transplanting the non-human monoclonal antibody variable domains, but "cloaking" them with a human-like surface by replacement of surface residues ("veneering"). These methods are disclosed, for example, in, e.g., Jones et al., Nature 321:522-525 (1986); Morrison et al., Proc. Natl. Acad. Sci., U.S.A., 81:6851-6855 (1984); Morrison and Oi, Adv. Immunol., 44:65-92 (1988); Verhoeyer et al., Science 239: 1534-1536 (1988); Padlan, Molec. Immun. 28:489-498 (1991); Padlan, Molec. Immunol. 31(3):169-217 (1994); and Kettleborough, C. A. et al., Protein Eng. 4(7):773-83 (1991).

To generate an antibody response, the isolated peptide of the present invention is typically formulated with a pharmaceutically acceptable carrier for parenteral administration. Such acceptable adjuvants include, but are not limited to, Freund's complete, Freund's incomplete, alum-precipitate, water in oil emulsion containing Corynebacterium parvum and tRNA. The formulation of such compositions, including the concentration of the polypeptide and the selection of the vehicle and other components, is within the skill of the art.

The term antibody as used herein is intended to include antibody fragments thereof which are selectively reactive with the peptides of the invention. Antibodies can be fragmented using conventional techniques, and the fragments screened for utility in the same manner as described above for whole antibodies. For example, F(ab')$_2$ fragments can be generated by treating antibody with pepsin. The resulting F(ab')$_2$ fragment can be treated to reduce disulfide bridges to produce Fab' fragments.

In a ninth aspect, the present invention provides polynucleotide primer pairs, comprising at least one forward primer and one reverse primer, wherein the combination of a forward primer and a reverse primer in the primer pair can be used to amplify expression products (mRNA or cDNA derived therefrom) comprising sequences encoding FDTTIGEKL (SEQ ID NO. 1).

In a tenth aspect, the present invention provides polynucleotide probes, comprising or consisting of polynucleotide probes that can be used to detect polynucleotide expression products (mRNA or cDNA derived therefrom) comprising sequences encoding FDTTIGEKL (SEQ ID NO. 1).

The primer pairs and probes of the ninth and tenth aspects of the invention can be used, for example, in the methods of the first, second, and third aspects of the invention. In a preferred embodiment, the polynucleotide primers of the ninth aspect or the polynucleotide probes of the tenth aspect of the invention are detectably labeled.

In an eleventh aspect, the present invention provides kits comprising one or more of the reagents of the fourth, fifth, sixth, seventh, eighth, ninth, or tenth aspects of the invention.

All embodiments of any aspect of the invention can be combined with other embodiments of any aspect of the invention unless the context clearly dictates otherwise.

Example 1

Objective

The objective of this study was to determine if Coccidioidal peptides and/or proteins could be detected in plasma from sero-positive dogs. The rationale for this work is that serological tests are not always able to identify infected dogs due to immunosuppression or a delayed immune response to the fungus. As such, the presence of Coccidioidal proteins or peptides in blood would provide confirm the presence of *Coccidioides* sp. and therefore provide a more definitive diagnosis of infection. Dogs were studied because they get infected and require serological testing and anti-fungal therapy just like humans, i.e., the tests and anti-fungal drugs are the same. It was hypothesized that peptides could be found from the fungus in the low molecular weight fraction of plasma from infected dogs.

Methods:

Blood was drawn from dogs who were clinically suspected to have Coccidioidomycosis. One tube of blood was sent to a veterinary laboratory for serological testing by ELISA to obtain CF (complement fixation antigen) titers. Plasma (1-2 ml) from another tube of blood was ultrafiltered and subjected to liquid chromatography-tandem mass spectrometry (LC-MS/MS) on a Thermo LTQ mass spectrometer. Mass spectra were searched against protein databases of *Coccidioides posadasii* str. *Silveira* and *Canis lupus* familiaris.

Results:

From 19 dogs clinically suspected of having coccidioidomycosis, 9 were seropositive, and 10 were seronegative. In the seropositive dogs, many peptides were identified corresponding to 59 different coccidioidal proteins and 136 canine proteins (See FIGS. 1-5). One coccidioidal peptide, FDTTIGEKL (SEQ ID NO. 1) was common among all 9 seropositive dogs. In the 10 seronegative dogs, FDTTIGEKL (SEQ ID NO. 1) was not found in 6 of the dogs, but it was detected in 4 of the dogs. Interestingly, FDTT peptide was not found in a seronegative dog that was on maintenance fluconazole therapy and previously seropositive.

Peptide FDTTIGEKL (SEQ ID NO. 1) appears to be derived from "hypothetical protein CPC735_066600 [*Coccidioides posadasii* C735 delta SOWgp]", Genbank accession number EER25560J. The sequence of this hypothetical protein is (SEQ ID NO. 2):

```
1  mappllnssn sfdakkpvty sttalkrwsc lnnnkdlpai
   pdvkaihvyd fdntlfnspl 61 pnpqlwnglt igflqayesf anggwwhdpn ilaatgqgid
   veeplawkgw wneqivelve
```

-continued

```
121  lsmkqkdvlt vlltgraess faeiikrivk srslefdlvc
     lkpeigpnsq rfsstinfkq 181  ifledmifty khadeirvye drirhvkgfr dyfeqfnlqf
     lapnshpirk sitaevihva 241  estrylppva eaaevqrmin shnaivtaas gnvtkspygr
     lrihrvifyt gymldnadse 301  rlvkyltlpm lspslvdsgd vklmantili tpraapkail
     drvggigkvv rwrvtdtavf 361  enkiwaarva pisdsediyt dnpdpvvvla lrrgarpidv
     grirnwnpvs eenalvfdtt 421  igeklvlrva ednsddgdge apnvgrpfkr rhkydtrdne
     dvpsypkenh repgrprggy 481  ndysrsrher hpddrpprhy hdedsrrgpp ppgyrgggrg
     ragrggrggr grgrapgpre 541  gggyagyrsl ddypssrpgy dgagddrggp gsgnpvmny
```

The peptide sequence is found in both strains, *C. immitis* and *C. posadasii*. There is no difference in clinical symptoms based on the strain with which one is infected.

Conclusions:

Coccidioidal peptides can be identified in plasma from dogs seropositive for coccidioidal CF antigen using LC-MS/MS techniques. Remarkably, one peptide was identified that was common in all 9 seropositive dogs. Although this peptide was detected in 4 of 10 seronegative samples, these dogs were all suspected of having canine coccidioidomycosis. Follow-up studies are planned with the seronegative dogs whose plasma contained this peptide. This suggests that LC-MS/MS can detect coccidioidal infection in dogs that are symptomatic and seropositive. Also postulated is that LC-MS/MS can detect coccidioidal peptides in symptomatic, but seronegative dogs due to delayed immune seroconversion.

Example 2

Figure 1:
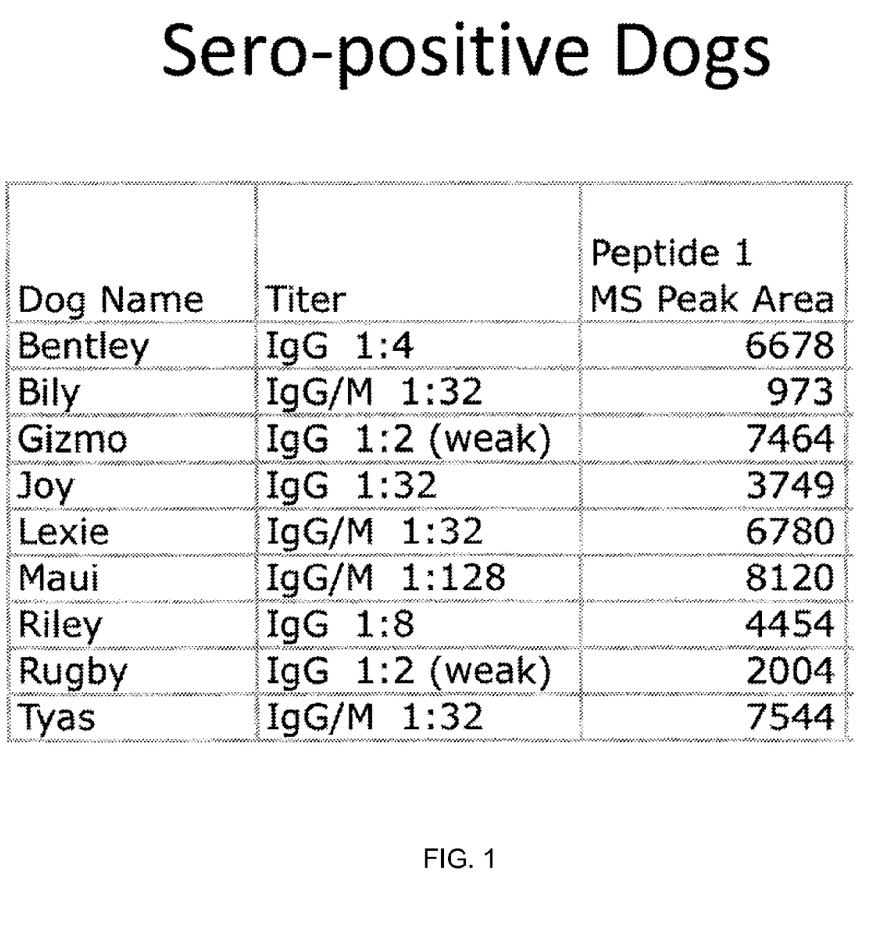
FIG. 1 depicts data from the studies in Example 1 from sera testing in dogs.
Figure 2:
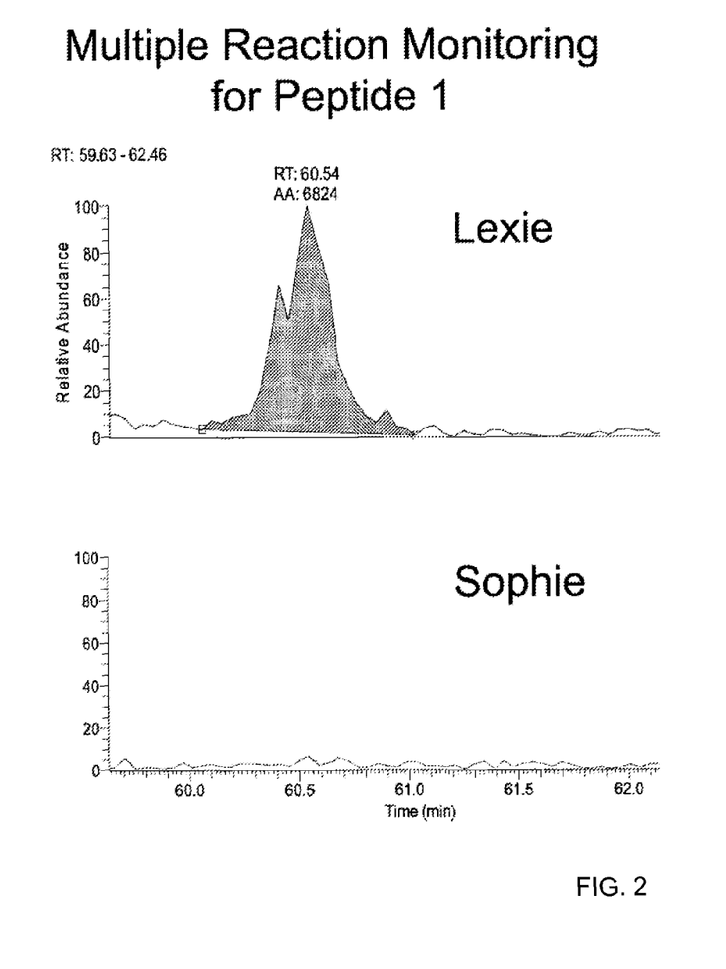
FIG. 2 depicts data from the studies in Example 1 from sera testing in dogs for a given peptide.
Figure 3:
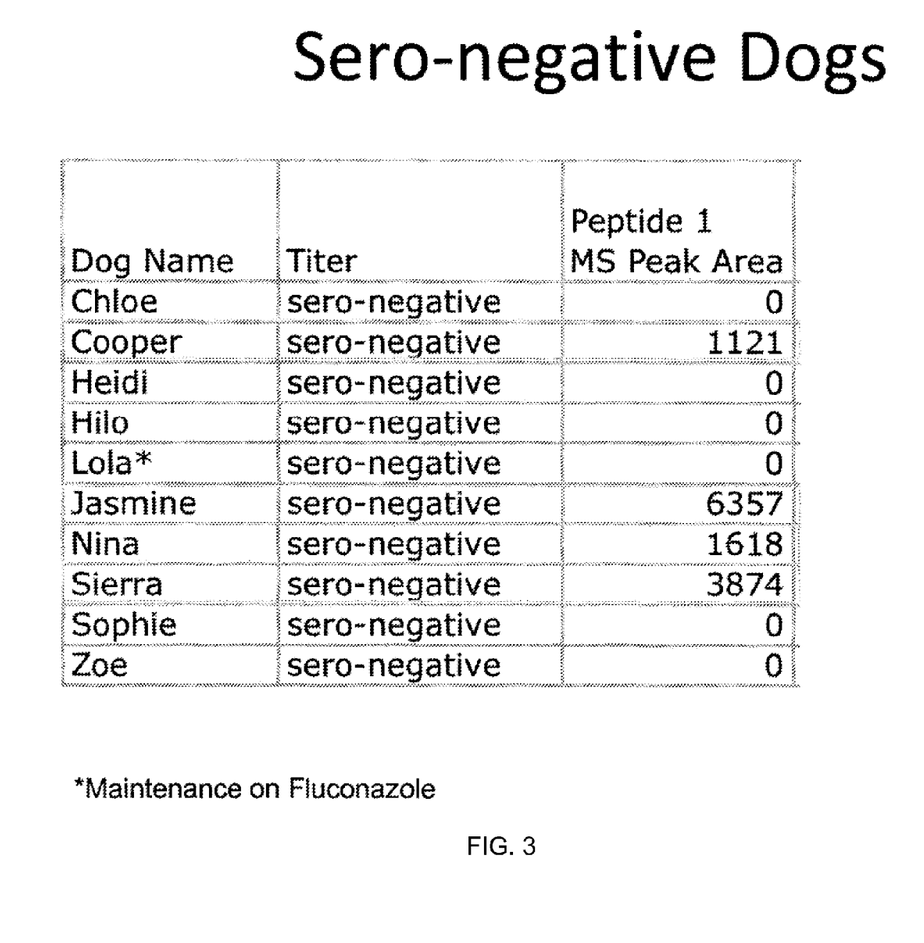
FIG. 3 depicts data from the studies in Example 1 from sero-negative dogs.
Figure 4:
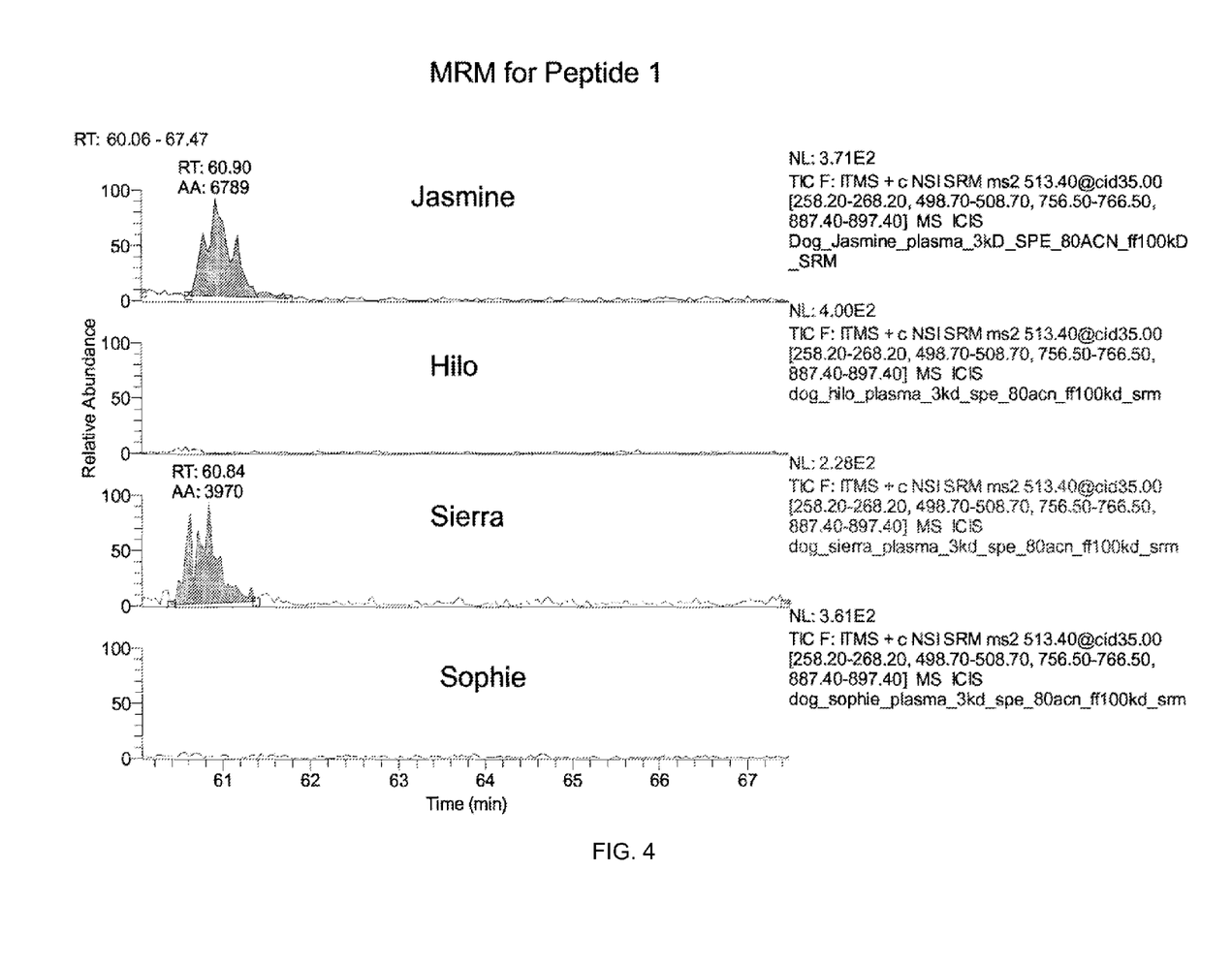
FIG. 4 depicts MRM data from the studies in Example 1 from sera testing in dogs.
Figure 5:
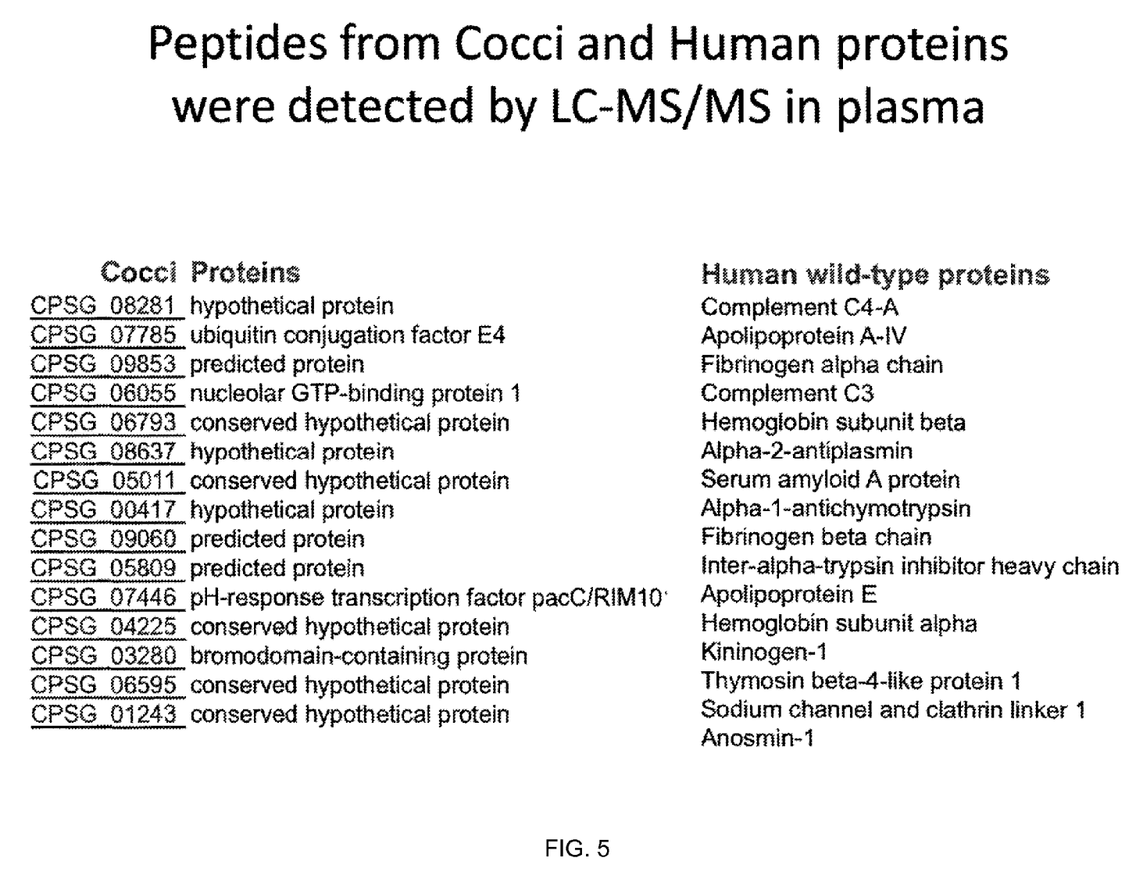
FIG. 5 depicts peptides from Cocci and human proteins detected in plasma.
Figure 6:
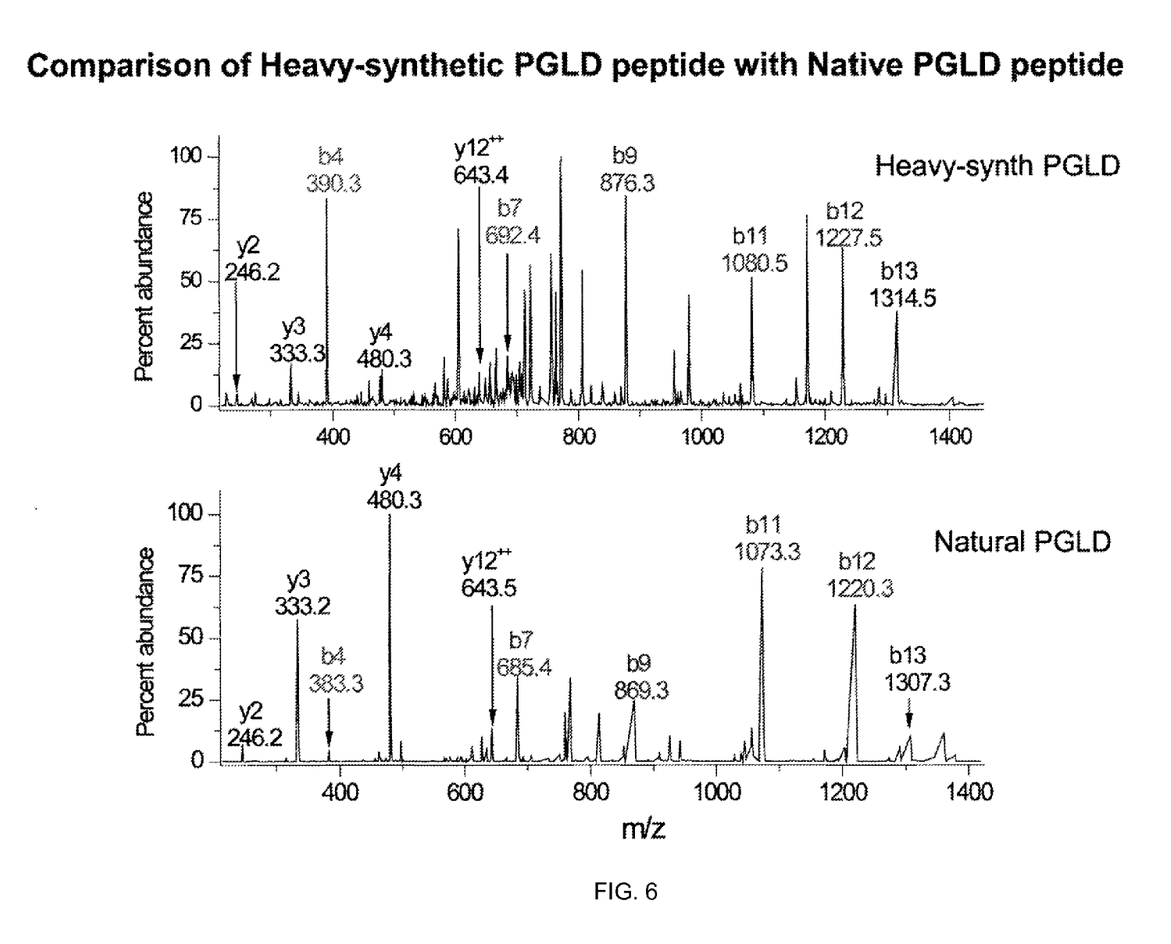
FIG. 6 depicts synthetic versus native peptide data from the studies in Example 2.
Figure 7:
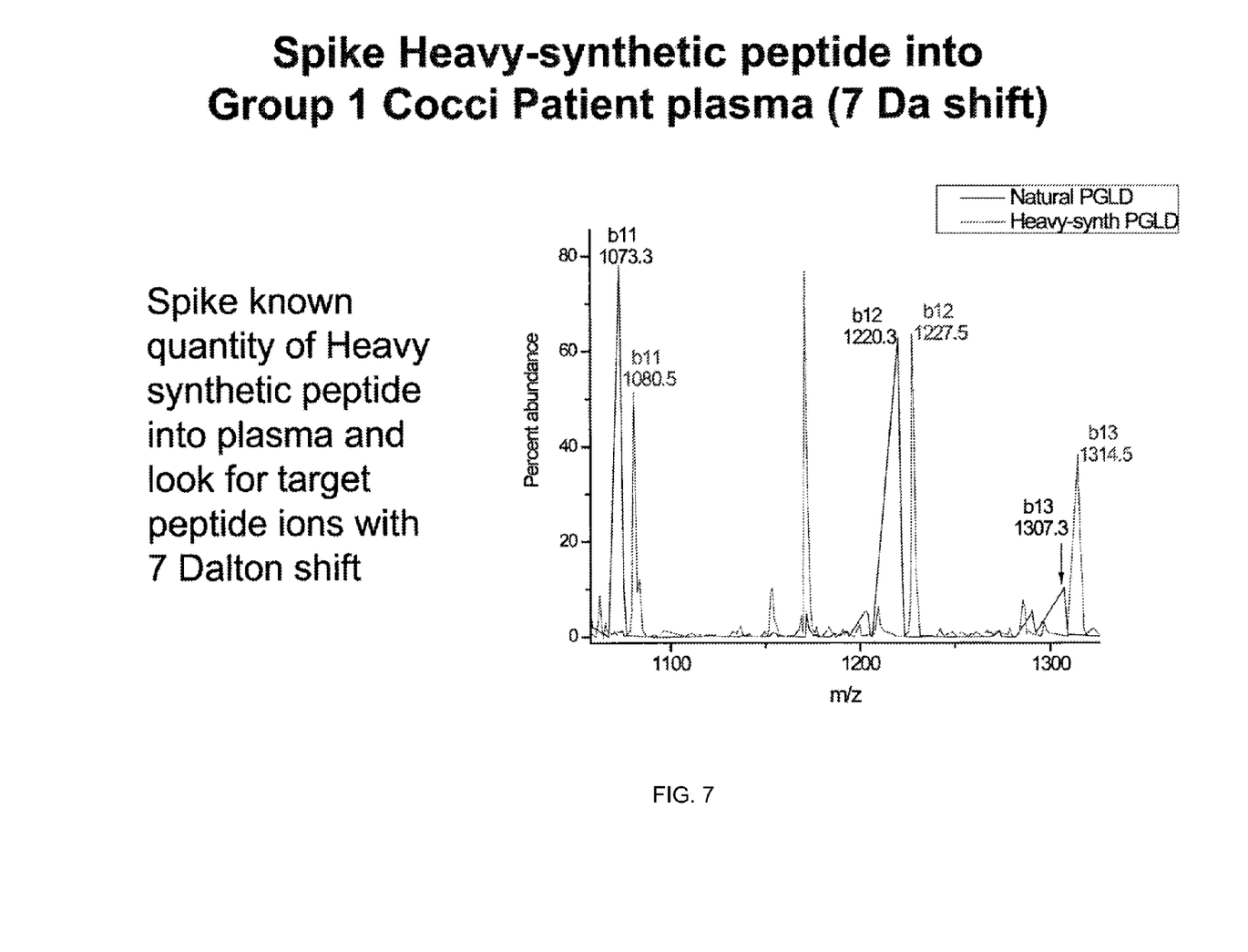
FIG. 7 depicts synthetic peptide spiking data from the studies in Example 2.
Figure 8:
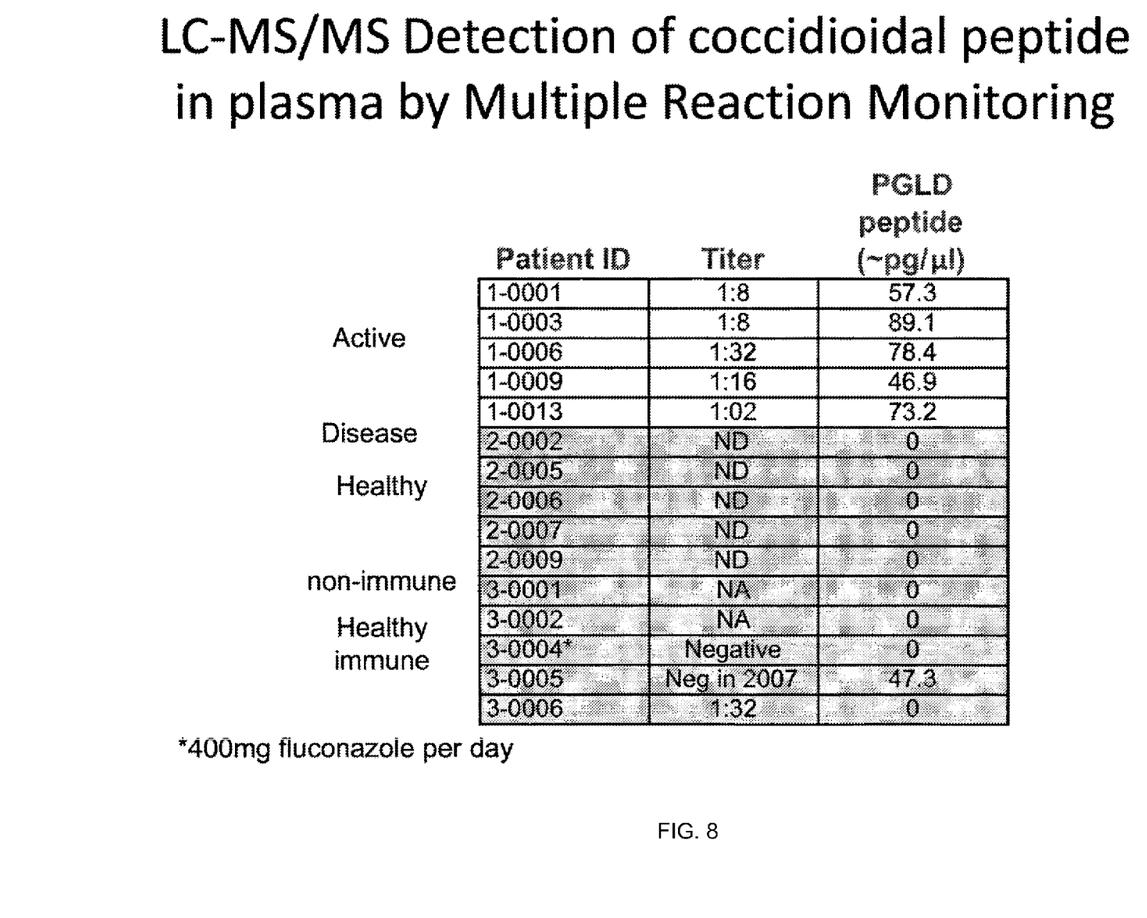
FIG. 8 depicts data from the studies in Example 2 from sera testing in humans.
Figure 9:
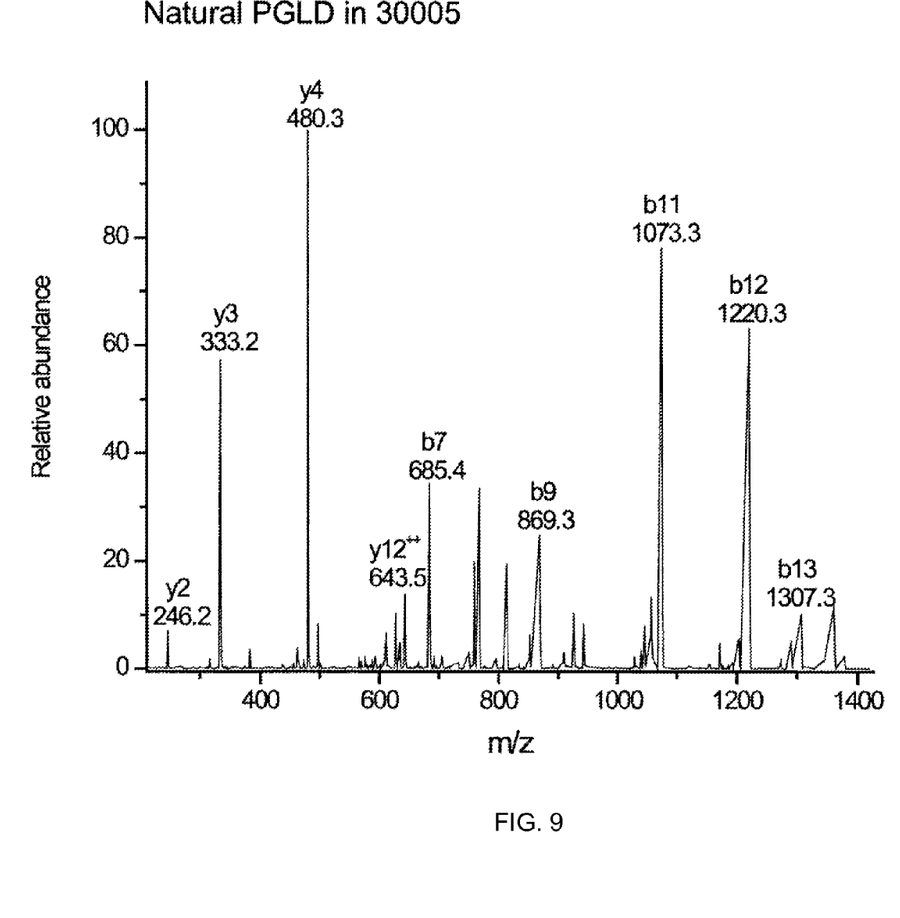
FIG. 9 depicts peptide data in a patient from the studies in Example 2.

A peptide with the sequence PGLDSKSLACTFSQV (SEQ ID NO. 4) was detected in plasma from over 15 human patients with active cases of Valley Fever, but this same peptide was not detected in plasma from 13 of 15 individuals who indicated they had never had Valley Fever (See FIGS. 5-9). To further validate the identity of the peptide, PGLDSKSLACTFSQV (SEQ ID NO. 4) was chemically synthesized with a "heavy leucine" in the fourth position such that the mass of the synthetic peptide is 7 daltons heavier than the natural plasma-derived peptide. This peptide was then spiked into plasma from patients with active disease followed by LC-MS/MS. SRM of the peptide ion fragmentation is shown in FIG. 6. The top spectra show b and y ion fragmentation of heavy PGLDSKSLACTFSQV (SEQ ID NO. 4) such that selected SRM peaks are 7 daltons heavier than the identical b and y ion peaks in the natural peptide in the bottom spectra. This assays allows the quantification of the natural peptide by establishing a standard curve with the heavy peptide that is chemically identical because the fragment ions are the same as the natural PGLDSKSLACTFSQV (SEQ ID NO. 4) peptide.

Example 3

Antibody levels against a component of the fungus are also used for monitoring patients during anti-fungal therapy. When titers against the fungus drop, the physician knows the patient's infection is resolving so that treatment can stop. However, some patients' antibody levels remain elevated, making it difficult to know when to stop treatment, even after 2 years. By monitoring the presence of a fungal antigen, a better indication for when patients may stop taking anti-fungal chemotherapy.

The distinct advantage of detecting and quantifying a component of the fungus in a body fluid such as blood is that a more definitive diagnosis can be made based on the presence of fungal proteins. In contrast, some patients' antibody responses against the fungus may be delayed or suppressed resulting in missed or delayed diagnosis and treatment.

We claim:

1. A method for diagnosing Coccidioidomycosis comprising testing a fluid sample from a subject at risk of Coccidioidomycosis for presence of a polypeptide comprising the amino acid sequence PGLDSKSLACTFSQV (SEQ ID NO: 4), wherein the method comprises
   a) contacting said sample from a subject at risk of Coccidioidomycosis with an antibody selective for a polypeptide comprising the amino acid sequence PGLDSKSLACTFSQV (SEQ ID NO: 4), under conditions to promote antibody binding to its selective antigen;
   b) removing unbound antibodies; and
   c) detecting antibody-antigen complexes.

2. The method of claim 1, wherein the method comprises testing a blood sample from a subject at risk of Coccidioidomycosis.

* * * * *